United States Patent [19]
Garito et al.

[11] Patent Number: 5,913,864
[45] Date of Patent: Jun. 22, 1999

[54] ELECTROSURGICAL DERMATOLOGICAL CURET

[76] Inventors: Jon C. Garito; Alan G. Ellman, both of 1135 Railroad Ave, Hewlett, N.Y. 11557

[21] Appl. No.: 08/871,707

[22] Filed: Jun. 9, 1997

[51] Int. Cl.$^6$ .................................................. A61B 17/50
[52] U.S. Cl. .............................. 606/131; 606/33; 606/45; 606/47
[58] Field of Search ................................. 606/131, 132, 606/160, 37, 39, 45, 47, 33

[56] References Cited

U.S. PATENT DOCUMENTS

| | | | |
|---|---|---|---|
| 4,534,347 | 8/1985 | Taylor | 606/33 |
| 4,657,016 | 4/1987 | Garito et al. | |
| 5,318,564 | 6/1994 | Eggers | 606/47 |

OTHER PUBLICATIONS

Dermatological Surgery, by Roenigk et al., published 1996 by Marcel Dekker, Inc. of New York, pp. 147–152.

Fundamentals of Cutaneous Surgery, by Bennett, published 1988 by The C.V. Mosby Co. of New York, pp. 250–253, 532–546.

Minor Surgery, 3rd Ed., by Brown, published 1997 by Chapman & Hall Medical, of New York, pp. 193, 212, 213.

*Primary Examiner*—Michael Buiz
*Assistant Examiner*—Julian W. Woo

[57] ABSTRACT

A novel electrode for use in an electrosurgical dermatological curretage procedure. It comprises a blade-shaped loop formed by folding a blade-shaped band to form at its center a generally circular loop with a sharpened edge. The electrode is uniquely configured to fit into a commercially available blade handpiece. The procedure using the electrode of the invention is based on performing essentially the same kind of dermatological excisions as was used heretofore but the structure of the electrosurgical electrode of the invention uses electrosurgical currents to excise or scoop out the diseased tissue and simultaneously electrocoagulates blood vessels and destroys any diseased tissue adjacent to and underlying the cavity or area that was curettaged.

11 Claims, 2 Drawing Sheets

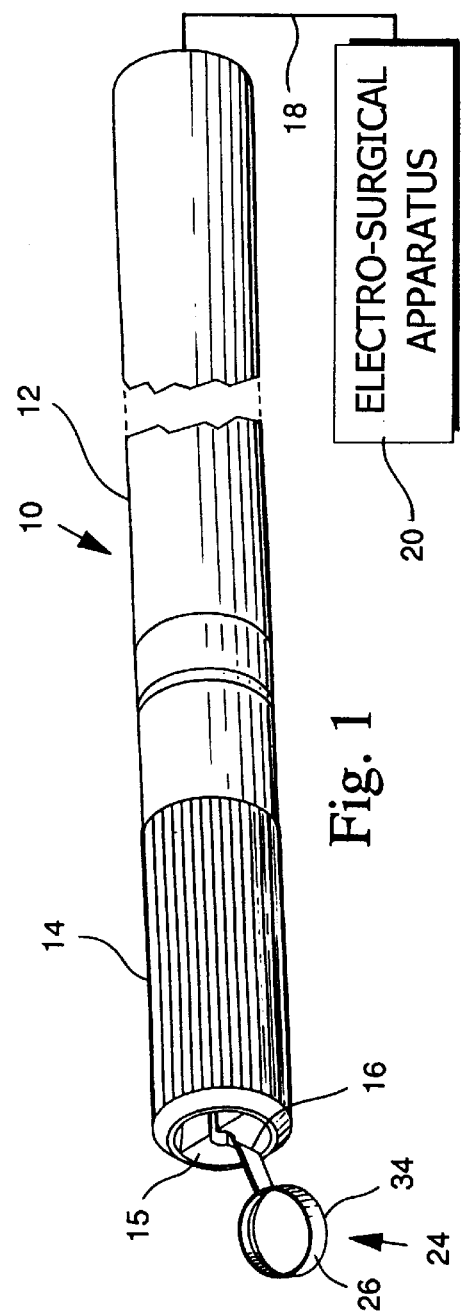
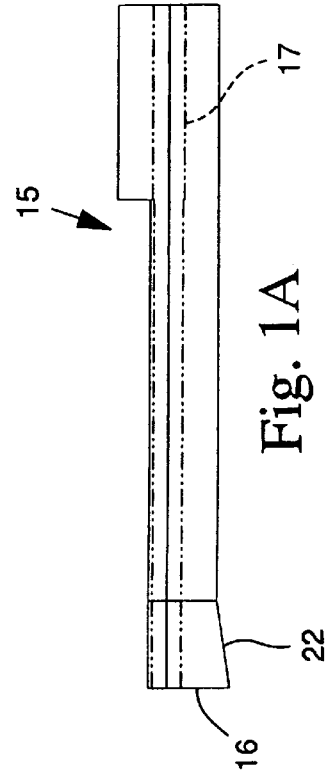
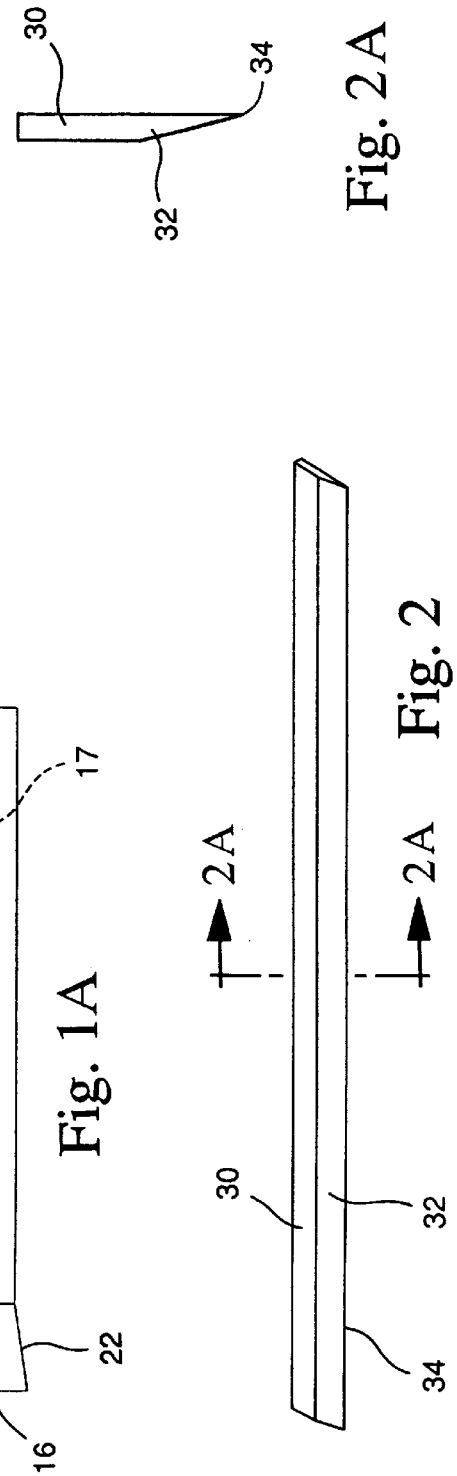

ELECTROSURGICAL DERMATOLOGICAL CURET

This invention relates to an electrosurgical instrument for curettage, and in particular, to an electrosurgical electrode for use in dermatological surgery.

BACKGROUND OF THE INVENTION

A dermatological curet is well known in the art and comprises a slender handle that fits into the hand and a round cutting edge in the form of a sharp oval or circular curet that can be used for scooping out cavities in tissue or small pockets of tumor and for small lesions. A sharp shearing force is used by the physician. It can also be used for treatment of superficial growths on the skin, both benign and malignant. The curet is typically held like a pencil in the hand of the physician, who balances and steadies the hand holding the curet with the little finger, which rests on the patient's skin. The thumb and index fingers of the opposite hand stretch the skin on which the curet is to be used. Thus, three point traction to the skin on which the lesion is to be curetted is achieved. This traction creates tension and a firm surface, which permit the physician to curette more easily through soft tissue. The firmer the surface, the better the curet works. Once tension on the skin is attained, the curet is drawn through the lesion and toward the physician with a steady yet firm downward scooping motion. This mechanical action literally scrapes the lesion from the adjacent normal tissue. This mechanical curetting is often followed by an electrosurgical treatment with a bipolar electrode to seal off bleeding blood vessels.

The disadvantage of a mechanical action curet is that the skin surface needs to be firm. It is difficult or impossible to use a mechanical curet on soft unsupported skin tissue such as the eyelid. A second disadvantage is that although mechanical curetting of skin to separate diseased tissue from normal surrounding tissue was described as early as 1876, skin surgeons remained unconvinced that the mechanical curetting of skin alone could cure carcinomas of the skin. Therefore other destructive methods were performed after the curettage. These methods included the use of caustics such as acid nitrate of mercury, radiation, electrosurgical techniques such as electrodesiccation or electrocoagulation, and liquid nitrogen (cryosurgery). The electrosurgical schemes frequently used a pointed electrode to destroy any tumor cells left behind following the mechanical curetting of the lesion.

SUMMARY OF THE INVENTION

An object of the invention is an improved dermatological curretting surgical procedure using an electrosurgical instrument, and a novel electrosurgical instrument for use in such a procedure, which can be used on soft unsupported skin.

Another object of the invention is an improved dermatological curretting surgical procedure using an electrosurgical instrument, and a novel electrosurgical instrument for use in such a procedure, which can be used without follow-up bleeding control or tissue destruction procedures.

We have invented a novel electrode for use in an electrosurgical dermatological curretage procedure. This electrosurgical procedure using our novel electrode enables physicians to offer to patients a treatment that is efficiently performed, easily learned and thus performed at a significantly reduced price. Moreover, there is less bleeding compared to procedures done with a mechanical curet, and no additional tissue destruction steps are required.

The procedure using our novel electrode is based on performing essentially the same kind of dermatological excisions as was used heretofore but, in accordance with a feature of our invention, the structure of our novel electrosurgical electrode uses electrosurgical currents to excise or scoop out the diseased tissue and simultaneously electrocoagulates blood vessels and destroys any diseased tissue adjacent to and underlying the cavity or area that was curettaged.

In accordance with another feature of our invention, the electrode of the invention is uniquely configured to fit into a commercially available blade handpiece which allows costs to be kept low.

The electrosurgical procedure has the important advantage of being able to scoop out the tissue with minimum surgeon pressure while at the same time coagulating the cut tissue causing minimum bleeding and destroying adjacent tissue. It is preferred that the electrosurgical currents used be above 1.5 MHz, and preferably above 2 MHz. At these high frequencies, commonly referred to as radiosurgery, cutting is accomplished by volatilizing intracellular fluids at the point of the transmitting electrode contact which is primarily responsible for only small lateral heat spread and thus less damage to neighboring healthy cell layers.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described the preferred embodiments of the invention, like reference numerals or letters signifying the same or similar components.

BRIEF DESCRIPTION OF THE DRAWINGS

In the drawings:

FIG. 1 is a perspective view of one form of electrosurgical instrument in accordance with the invention, shown connected to electrosurgical apparatus;

FIG. 1A is a side view of a collet used in the handpiece of FIG. 1;

FIG. 2 is a perspective view of a sharpened band which when folded forms one form of electrode in accordance with the invention;

FIG. 2A is a cross-sectional view along the line 2A—2A of FIG. 2;

DETAILED DESCRIPTION OF THE PREFERRED EMBODIMENTS

Figure 3:
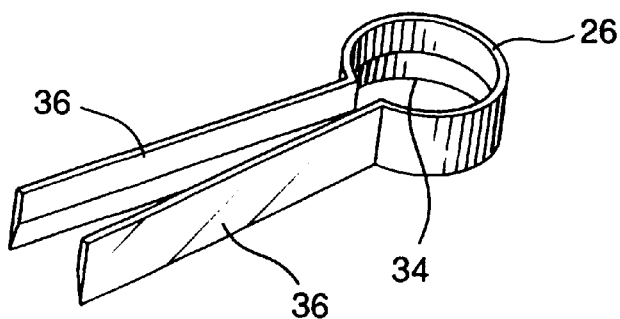
FIGS. 3 and 4 are perspective views of variants of the electrosurgical electrode according to the invention produced when the band of FIG. 2 is folded.

FIG. 1 illustrates a preferred form of the novel electrosurgical instrument 10 of the invention. It comprises an elongated conventional blade handpiece 12 of electrically-insulating material comprising a generally cylindrical body with a rotatable nosepiece 14 enclosing a brass collet 15 having a slitted front 16 and internal thread 17 threadingly engaging a threaded stud (not shown) in the fixed part of the handpiece and extending throughout its length and connected at its end to a cable 18 which is connected in the conventional manner to conventional electrosurgical apparatus 20. As an example only, the electrosurgical apparatus 20 can be model AAOP Surgitron FFPF available from Ellman International, Inc. of Hewlett, N.Y. The Ellman equipment is preferred due to its high operating frequency, typically above 1.5 MHz, preferably above 2 Mhz. This particular apparatus provides electrosurgical currents at 3.8 MHz. The blade handpiece 12 is also available from Ellman International, Inc. of Hewlett, N.Y. as Model H15. The latter is also described in a commonly owned U.S. Pat. No. 4,657,016, whose contents are herein incorporated by reference. As described therein in connection with FIGS. 11A and 11B, the collet 15, also illustrated herein in Fig. 1A, comprises an outwardly-tapered front end 22 which when drawn into the nosepiece 14 when the latter is rotated closes down on the slitted front 16 so that it will firmly grip, for example, a flat surgical blade or razor blade inserted in the slit. The curet electrode of the invention is configured to be used with the blade handpiece 12 described in the patent or a similarly configured handpiece capable of receiving and gripping a blade-shaped electrode end.

At the collet end of the handpiece 12 is mounted one form of an electrosurgical electrode 24 according to the invention, which comprises a electrically-conductive generally ring-shaped scooping end 26, mounted at its end nearest the handpiece 12 in the handpiece collet slit 16 and thus electrically connected to the electrically-conductive cable 18. The electrode 24 is shown tilted downward so that the longitudinal axis of its blade end is at an angle of about 30° with respect to the longitudinal axis of the handpiece 12. An advantage of the blade handpiece 12 with its vertical slit 16 is that the electrode 24 can be positioned in line with the handpiece axis, or tilted downward as illustrated in FIG. 1 and gripped firmly in either or any intermediate positions when the rotatable nosepiece 14 is tightened. To remove the electrode 24 or reposition the electrode merely requires that the nosepiece 14 is loosened, the electrode removed or repositioned, and the nosepiece then tightened.

Figure 4:
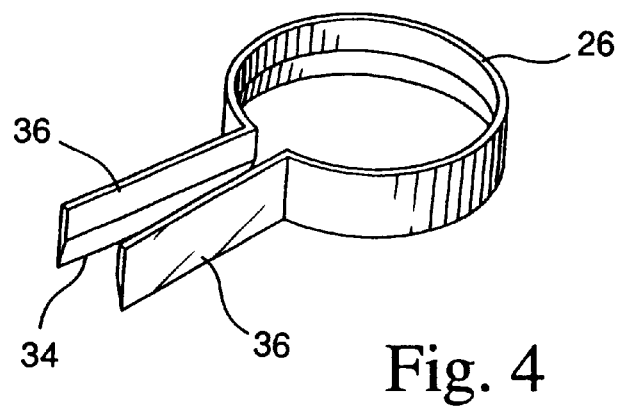
Figure 5:
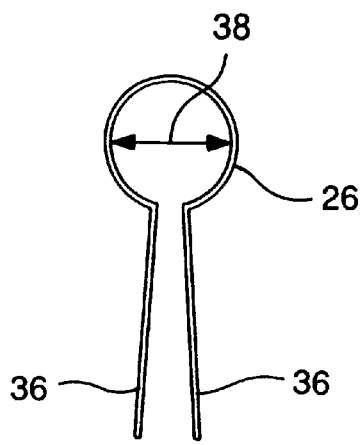
FIG. 5 is a plan view of still another variant.

The scooping end 26 of the electrode 24 comprises a band-shaped generally circular cutting member, for example of stainless steel, and is inexpensively formed by starting from a straight or unfolded metal band 30 as illustrated in FIG. 2 with its lower half 32 sharpened. Typical dimensions are a height of about 1.5–2.5 mm, preferably 2.0 mm, and a length of about 30–40 mm, preferably 35 mm. A typical thickness of the band is about 0.2–0.3 mm, preferably 0.25 mm, and as mentioned, the lower half 32 is sharpened along its full length to a fine edge 34. The band 30 is then folded or bent around a mandrel to form as shown in FIG. 3 a circular loop 26 with two straight extension arms 36. For removing different sized lesions, it is convenient to have available a family of electrodes of different sizes, such as with a loop diameter of 4, 5, and 7 mm. The loop diameter is shown at 38 in the plan view of FIG. 5. The same initial length of band 30 can be used for all three folded shapes, and as will be noted from the second larger loop electrode shown in FIG. 4, as the loop 26 gets larger, the extension arms 36 shrink but remain sufficiently long to be received within the slitted front end 16 of the gripping collet 15 of the handpiece. For instance, starting with a 35 mm length blade 30, for the 4 mm loop, the arm extensions 36 would have a length of about 11.2 mm, whereas for the 7 mm loop, the arm extensions 36 would have a length of about 6.5 mm. Both of the arm extensions 36 are brought together and inserted into the collet slit 16 of the handpiece 12 when the nosepiece 14 is loosened. It is noted that, though the blade handpiece 12 was originally designed to accept the single blade end of a surgical blade, it works quite satisfactorily with the bifurcated end of the scooping electrode of the invention, thus making the design and construction of a new handpiece construction unnecesary.

During the performance of a curettage procedure on a patient, also connected to the electrosurgical apparatus 20 is the usual indifferent plate (not shown) which during use is in contact with the patient's body. When the electrosurgical apparatus 20 is energized, high frequency electrosurgical currents are generated which are coupled by way of the cable 18 and electrically-conductive collet 15 to the active, bare cutting loop 26. The physician, in the usual way, holds the handpiece 12 while applying the fine edge 34 of the active working loop end 26 of the electrode to the desired skin area of the patient to be treated. When activated, the active loop 26 cuts cleanly and easily with little pressure required through the tissue to be excised. The novel curet blade lop 24 mounted on the blade handpiece 12 allows the curet smooth movement through the skin tissue without pressure or crushing cells. Stretching of the skin by the physician is unnecessary. The curet electrode 24 simultaneously destroys the diseased tissue superficially as it is being scooping out. Bleeding is also controlled due to the R.F. electrosurgical currents being introduced through the energized curet blade 26.

With the Ellman equipment, the fully rectified or cut/coag current is used at a power setting of about 3–4 with the active loop electrode 24. There is very little trauma and the sore area felt by the patient at the excised site is easily handled by analgesia and anti-inflammatory drugs.

It will also be understood that, though the electrode of the invention is specifically designed for dermatological surgical treatments, it is not limited to its use for such procedures. To those skilled in this art, there will certainly be other uses for this novel electrode that provides a blade-shaped generally circular active cutting end that is conveniently used with the commercially available blade handpiece. It will also be understood that, though the electrode of the invention has been described for dermatological surgical treatments on humans, it is not limited to its use for such procedures and can also be used for similar purposes by other practitioners, such as on animals by veterinarians.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. An electrosurgical electrode for excising of tissue, comprising:
   (a) an electrically conductive member having a generally blade-shaped first end for mounting to a handpiece and an active cutting second end,
   (b) said active second end comprising a generally loop-shaped blade having a sharpened inside edge, the active second end having a generally circular shape with a diameter between about 4 and 7 mm,
   (c) said active second end being exposed electrically for applying electrosurgical currents to said tissue when said first end is connected to a source of electrosurgical currents.

2. An electrosurgical electrode for excising of tissue, comprising:
   (a) an electrically-conductive member having a generally blade-shaped first end for mounting to a handpiece and an active cutting second end,
   (b) said active second end comprising a generally loop-shaped blade having a sharpened edge,
   (c) said active second end being exposed electrically for applying electrosurgical currents to said tissue when said first end is connected to a source of electrosurgical currents, (d) the electrically-conductive member comprising a one-piece blade-shaped body folded to form two generally parallel arms, constituting the first end, extending from a central loop constituting the active second end.

3. An electrosurgical electrode as claimed in claim 2, wherein the blade-shaped body has a longitudinal dimension and is sharpened along one half of its longitudinal dimension.

4. In combination:
   (a) a blade handpiece having means at one end for connection to electrosurgical apparatus capable of supplying high frequency currents and having at its opposite end means for receiving and gripping the electrically-conductive first end of an electrosurgical electrode and for supplying the high frequency currents to said electrode;
   (b) an electrosurgical electrode for excising of tissue, comprising:
      (i) an electrically-conductive member having a generally blade-shaped first end for mounting to the handpiece and an active cutting second end,
      (ii) said active second end comprising a generally loop-shaped blade having a sharpened inside edge, the active second end having a generally circular shape with a diameter between about 4 and 7 mm,
      (iii) said active second end being exposed electrically for applying electrosurgical currents to said tissue when said electrode is mounted in the handpiece and the electrosurgical apparatus activated.

5. The combination as claimed in claim 4, wherein the electrically-conductive member comprises a one-piece blade-shaped body folded to form two generally parallel arms, constituting the first end, extending from a central loop constituting the active second end.

6. In combination:
   (a) a blade handpiece having means at one end for connection to electrosurgical apparatus capable of supplying high frequency currents and having at its opposite end means for receiving and gripping the electrically-conductive first end of an electrosurgical electrode and for supplying the high frequency currents to said electrode wherein the blade handpiece comprises a collet having a vertical slit for receiving the first end of the electrode;
   (b) an electrosurgical electrode for excising of tissue, comprising:
      (i) an electrically-conductive member having a generally blade-shaped first end for mounting to the handpiece and an active cutting second end,
      (ii) said active second end comprising a generally loop-shaped blade having a sharpened edge,
      (iii) said active second end being exposed electrically for applying electrosurgical currents to said tissue when said electrode is mounted in the handpiece and the electrosurgical apparatus activated.

7. An electrosurgical electrode for excising of tissue, comprising:
   (a) an electrically-conductive member having a generally blade-shaped first end for mounting to a handpiece and an active cutting second end,
   (b) said active second end comprising a generally band-shaped looped blade having a generally circular upper edge and a lower inside edge,
   (c) the generally circular lower inside edge of said active second end being exposed electrically for applying electrosurgical currents to said tissue when said first end is connected to a source of electrosurgical currents,
   (d) the generally circular lower inside edge being sharpened such that tissue surrounded by the generally circular lower inside edge can be scooped out when the band is pulled along the tissue with the sharpened edge contacting the tissue while electrosurgical curents are applied to the band.

8. In combination:
   (a) a blade handpiece having means at one end for connection to electrosurgical apparatus capable of supplying high frequency currents and having at its opposite end means for receiving and gripping the electrically-conductive first end of an electrosurgical electrode and for supplying the high frequency currents to said electrode;
   (b) an electrosurgical electrode for excising of tissue, comprising:
      (i) an electrically-conductive member having a generally blade-shaped first end for mounting to the handpiece and an active cutting second end,
      (ii) said active second end comprising a generally band-shaped looped blade having a generally circular upper and a lower inside edge,
      (iii) the generally circular lower inside edge of said active second end being exposed electrically for applying electrosurgical currents to said tissue when said first end is connected to a source of electrosurgical currents,
      (iv) the generally circular lower inside edge being sharpened such that tissue surrounded by the generally circular lower inside edge can be excised when the band is pulled along the tissue with the sharpened edge contacting the tissue while electrosurgical curents are applied to the band.

9. The combination of claim 8, further comprising electrosurgical apparatus capable of supplying high frequency electrosurgical currents wherein the high frequency currents are at a frequency exceeding 1.5 Mhz.

10. A dermatological curettage surgical procedure for removing a lesion from a patient, comprising the steps:
   (a) providing electrosurgical apparatus connected to a handpiece holding an electrosurgical electrode, said electrosurgical electrode comprising:
      (i) an electrically-conductive member having a generally blade-shaped first end for mounting to the handpiece and an active cutting second end,
      (ii) said active second end comprising a generally loop-shaped blade with a generally circular upper and a lower inside edge, the generally circular lower inside edge being sharpened,
      (iii) said active second end being exposed electrically for applying electrosurgical currents to tissue of the patient when said electrode is mounted in the handpiece and the electrosurgical apparatus activated,
   (b) applying the sharpened lower inside edge to tissue of the patient where the lesion is located so as to surround the lesion and activating the electrosurgical apparatus,
   (c) pulling forward the energized sharpened lower inside edge and scooping out the lesion while simultaneously using the electrosurgical currents to control any bleeding and destroy any diseased tissue superficially while scooping.

11. The dermatological curettage surgical procedure as claim 10, wherein the electrosurgical currents are at a frequency exceeding 1.5 MHz.

* * * * *

UNITED STATES PATENT AND TRADEMARK OFFICE
Certificate

Patent No. 5,913,864                                                                  Patented: June 22, 1999

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Orin M. Goldblum, Pittsburgh, PA; Jon C. Garito, Hewlett, NY; and Alan G. Ellman, Hewlett, NY.

Signed and Sealed this Ninth Day of September 2003.

HENRY J. RECLA
*Supervisory Patent Examiner*
Art Unit 3731